US008152986B2

(12) United States Patent
Deniau et al.

(10) Patent No.: US 8,152,986 B2
(45) Date of Patent: Apr. 10, 2012

(54) PROCESS FOR FORMING ORGANIC FILMS ON ELECTRICALLY CONDUCTIVE OR SEMI-CONDUCTIVE SURFACES USING AQUEOUS SOLUTIONS (75) Inventors: Guy Deniau, Auffargis (FR); Serge Palacin, Montigny le Bretonneux (FR)

(73) Assignee: Commissariat a l'Energie Atomique (FR)

( * ) Notice: Subject to any disclaimer, the term of this patent is extended or adjusted under 35 U.S.C. 154(b) by 933 days.

(21) Appl. No.: 11/364,360

(22) Filed: Feb. 28, 2006

(65) Prior Publication Data
US 2007/0289872 A1 Dec. 20, 2007

(51) Int. Cl.
C25D 11/00 (2006.01)
(52) U.S. Cl. ........................................... 205/317
(58) Field of Classification Search .................. 205/317
See application file for complete search history.

(56) References Cited

U.S. PATENT DOCUMENTS

| 4,724,053 | A  | * | 2/1988 | Jasne .............................. 106/236 |
| 7,182,822 | B2 | * | 2/2007 | Pinson et al. ................... 148/241 |
| 2006/0141156 | A1 | * | 6/2006 | Viel et al. ....................... 427/258 |

FOREIGN PATENT DOCUMENTS

WO  WO 0159178 A1 * 8/2001
WO  WO 2004074537 A1 * 9/2004

OTHER PUBLICATIONS

Koval'chuk et al., "Reduction of Diazonium Salts on a Copper Cathode in the Presence of Acrylamide", Zhurnal Obshchei Khimii (no month, 1992), vol. 52, No. 11, pp. 2540-2543.*
Bravo-Diaz et al., "Effects of Monovalent and Divalent Anionic Dodecyl Sulfate Surfactants on the Dediazoniation of 2-, 3-, and 4-Methylbenzenediazonium Tetrafluoroborate", Langmuir (no month, 1998), vol. 14, pp. 5098-5105.*
Zana, "Microviscosity of Aqueous Surfactant Micelles: Effect of Various Parameters", J. Phys. Chem. B (no month, 1999), vol. 103, pp. 9117-9125.*
Tidswell et al., "Electroinitiated Emulsion Polymerisation of Vinyl Acetate", Br. Polym. J. (no month, 1975), vol. 7, pp. 409-416.*
Tidswell et al., "Electroinitiated Emulsion Polymerisation of Vinyl Acetate. I. The Mechanism of Initiation", Br. Polym. J. (no month, 1975), vol. 7, pp. 409-416.*
French, "Mechanism of Vinyl Acetate Emulsion Polymerization", J. of Polymer Science (no month, 1958), vol. XXXII, pp. 395-411.*
Downard, "Potential-Dependence of Self-Limited Films Formed by Reduction of Aryldiazonium Salts at Glassy Carbon Electrodes", Langmuir (no month, 2000), vol. 16, pp. 9680-9682.*

* cited by examiner

Primary Examiner — Edna Wong

(74) Attorney, Agent, or Firm — Alston & Bird LLP (57) ABSTRACT

The present invention concerns the area of surface coatings in the form of organic films, the coatings being in the form of organic films. It most especially relates to a method for forming copolymer organic films by electrochemical grafting on electrically conductive or semi-conductive surfaces using electrolytic aqueous solutions containing at least one protic solvent, at least one radically polymerizable monomer and at least one surfactant. The invention also concerns surfaces obtained with the use of this method, their applications especially for preparation of microelectronic components, biomedical devices or screening kits, as well as the electrolyte solution used in the course of the method.

17 Claims, 6 Drawing Sheets

PROCESS FOR FORMING ORGANIC FILMS ON ELECTRICALLY CONDUCTIVE OR SEMI-CONDUCTIVE SURFACES USING AQUEOUS SOLUTIONS

FIELD AND BACKGROUND OF THE INVENTION

The present invention concerns the area of surface coatings, the said coatings being in the form of organic films. It relates specifically to a method for forming copolymer organic films by electrochemical grafting on electrically conductive or semi-conductive surfaces using aqueous solutions of precursors that are appropriately selected in order to permit the formation of these organic films in a simple and reproducible manner on the surfaces obtained by using this method, and to their applications, in particular for preparation of microelectronic components, biomedical devices or screening kits.

At the present time, several techniques exist that make it possible to apply thin organic films on substrates, each based on a family or class of adapted molecules.

The method for forming a coating using centrifuging known by the English name "spin coating" or the techniques included in the formation of coatings by immersion ("dip coating") or deposit by vaporizing ("spray coating") do not require any specific affinity between the molecules deposited and the substrate of interest. In fact, the cohesion of the deposited film is based essentially on the interaction between the constituents of the film, which may be, e.g., cross-linked after they are deposited to improve stability. These techniques are very versatile, applicable to all types of surfaces to be covered, and are very reproducible. However, they do not permit any effective grafting between the film and the substrate (it is a case of simple physisorption), and the thicknesses produced are difficult to control, especially for the finest deposits (less than 20 nanometers). In addition, the spin coating techniques do not allow uniform deposits unless the surface to be covered is essentially flat. The quality of the films obtained by the techniques of "spray coating" is connected with wetting of the surfaces by the powdered liquid, since the deposit does not essentially become film-like until the drops coalesce. Thus, for a given polymer, generally only one or two organic solvents exist that are capable of yielding satisfying results in terms of controlling the thickness and the homogeneity of the deposit.

Other techniques for forming an organic coating on the surface of a support, such as deposition by plasma, are described, for example, in the articles by M. Konuma, "*Film deposition by plasma techniques*," (1992) Springer Verlag, Berlin; H. Biederman and Y. Osada, "*Plasma polymerization processes,*" 1992, Elsevier, Amsterdam, or even photochemical activation based on a similar principle: producing unstable forms of a precursor close to the surface to be covered, which evolves by forming a film on the substrate. While deposition by plasma does not require any specific properties of these precursors, photo-activation requires the use of photosensitive precursors, of which the structure evolves under the influence of luminous radiation. These techniques generally give rise to the formation of adherent films, even though it is usually impossible to discern whether this adhesion is due to cross-linking of a topologically closed film around the object or a real formation of interface bonds.

Auto-assembly of monolayers is a very simple technique to use (A. Ulman, "*An introduction to ultrathin organic films from Langmuir-Blodgett films to self-assembly,*" 1991, Boston, Academic Press). Still, this technique generally requires the use of molecular precursors having an adequate affinity for the surface of interest to be coated. We then speak of the precursor-surface pair such as the sulfur compounds that have an affinity for gold or silver, the tri-halogen silanes for oxides like silica or aluminum, and the polyaromatics for graphite or nanotubes of carbon. In all cases, the formation of the film is based on a specific chemical reaction between a part of the molecular precursor (the sulfur atom in the case of thiols, for example) and certain "receptor" sites on the surface. A chemisorption reaction ensures bonding. Thus, at ambient temperature and in solution, films with molecular thickness (less than 10 nm) are obtained. However, while the pairs involving oxide surfaces give rise to the formation of films that are very tightly grafted (the Si—O bond involved in the chemisorption of the tri-halogen silanes on silica is among the most stable in chemistry), this is of no use when there is an interest in metals or semi-conductors without oxide. In this case, the bond of the interface between the conductive surface and the monomolecular film is fragile. Thus, auto-assembled monolayers of thiols on gold desorb when they are heated above 60° C. or in the presence of a good solvent at ambient temperature, or even when they come in contact with a liquid oxidizing or reducing medium. In a similar manner, the Si—O—Si bonds are weakened when they are in an aqueous medium, i.e., humidity, especially with the effect of heat.

Electrografting of polymers is a technique based on initiation then polymerization by propagation of an electrically induced chain of electroactive monomers on the surface of interest, playing simultaneously the role of electrode and that of a polymerization primer (S. Palacin et al., "*Molecule-to-metal bonds: electrografting polymers on conducting surfaces.,*" Chem Phys Chem, 2004, 10, 1468). Electrografting requires the use of precursors that are adapted to this mechanism of initiation by reduction and propagation, generally anionic, since sometimes electrografting that is cathodically initiated is preferred, which is applicable to noble metals and non-noble metals (in contrast to electrografting by anodic polarization, which is not applicable except to noble substrates). "Depleted vinyl" molecules, i.e., carriers of functional electro-attractor groups like the acrylonitriles, the acrylates, the vinyl pyridines, etc., are especially adapted to this method, which gives rise to a number of applications in the area of microelectronics in the biomedical area. The adherence of the electrografted films is ensured by a carbon-metal type covalent bond (G. Deniau et al., "*Carbon-to-metal bonds: electrochemical reduction of 2-butenenitrile,*" Surface Science, 2006, 600, 675-684).

According to this electrografting technique, polymerization is indispensable for the formation of the carbon/metal interface bond: it has actually been shown (G. Deniau et al., "*Coupled chemistry revisited in the tentative cathodic electropolymerization of 2-butenenitrile.,*" Journal of Electroanalytical Chemistry, 1998, 451, 145-161) that the electrografting mechanism proceeds due to an electroreduction of the monomers on the surface to yield an unstable radical anion, which, if it is not present in the medium of polymerizable molecules, desorbs to return to solution (op. cit.). This desorption reaction, the addition reaction (of the Michael addition type) of the charge of the first chemisorbed radical anion on a free monomer, offers a second means for stabilizing the reaction intermediary: the product of this addition yields a radical anion again but where the charge is "at a distance from" the surface, which contributes to stabilizing the adsorbed structure. This dimeric radical anion itself may again be added to a free monomer, and thus the consequence: each new addition has additional stability by relaxation of the charge/polarized surface repulsion, which means that the interface connection of the first radical anion temporarily becomes stable to the extent that the polymerization has taken place. In other words, it has been claimed that a vinyl monomer that cannot be polymerized cannot be electro-grafted.

Among the different techniques mentioned above, electrografting is the only technique that makes it possible to produce grafted films with a specific control of the interface bond. In addition, in contrast to the plasma or photo-induced techniques, electrografting does not generate reactive species except in the immediate area of the surface of interest (in the double electrochemical layer, of which the thickness is of several nanometers in the majority of cases).

It now seems that obtaining grafted polymer films by electrografting of activated vinyl monomers on electrically conductive surfaces proceeds due to an electro-initiation of the polymerization reaction starting from the surface, followed by a growth in the chains, monomer by monomer. The reaction mechanism of electrografting has been described, in particular, in the articles of C. Bureau et al., Macromolecules, 1997, 30, 333; C. Bureau and J. Delhalle, Journal of Surface Analysis, 1999, 6(2), 159 and C. Bureau et al., Journal of Adhesion, 1996, 58, 101.

By way of example, the electrografting reaction mechanism of acrylonitrile by cathodic polarization can be represented by Diagram A following:

polarization of the conductive surface that has given rise to the grafting. This step is thus sensitive to (and is in particular interrupted by) the presence of chemical inhibitors of this growth, in particular by protons.

In Diagram A above, where electrografting of acrylonitrile using cathodic polarization is considered, the growth of the grafted chains is carried out by anionic polymerization. This growth is interrupted, in particular, by protons and it has also been demonstrated that the amount of protons makes up the major parameter that guides the formation of polymers in solution; information obtained in the course of synthesis, especially the speed of voltammograms that accompany the synthesis, show this (see in particular the article by C. Bureau, Journal of Electroanalytical Chemistry, 1999, 479, 43). Traces of water, and more generally unstable protons of protonic solvents, make up the sources of protons that are detrimental to the growth of the grafted chains.

Overall, while way to produce chemical bonds on electrically conductive or semi-conductive substrates by electrografting of different precursors using organic solutions is known, because of these reactions it remains difficult to obtain films using aqueous solutions since the adjacent reaction mechanisms (anionic-type polymerization) do not make it possible to work in water. Up to the present time, only aryl diazonium salts have made it possible to approach a solution to this problem.

DIAGRAM A

1: Réaction chimique de surface, greffage

2: Désorption, polymérisation en solution

Key:
1: Réaction chimique de surface, greffage = Chemical surface reaction, grafting
2: Désorption, polymerization en solution = Desorption, polymerization in solution In this diagram, the grafting reaction corresponds to step 1, where the growth takes place starting from the surface. Step 2 is the principal parasitic reaction, which leads to obtaining a non-grafted polymer; this reaction is limited by the use of strong monomer concentrations.

The growth of the grafted chains is thus carried out by purely chemical polymerization, i.e., independently of the Thus, as described, e.g., in the French patent application FR-A-2 804 973, electrografting of precursors such as aryl diazonium salt that carry a positive charge can be carried out due to a cleavage reaction after reduction of the cation to yield a radical that chemisorbs on the surface. Just as in electrografting of polymers, the electrografting reaction of aryl diazonium salts is electro-initiated and leads to the formation of interface chemical bonds. In contrast, to the electrografting reactions of vinyl polymers, the electrografting of aryl diazonium salts does not "need" a coupled chemical reaction to stabilize the chemisorbed species formed as a result of transfer of charge since this species is electrically neutral and not charged negatively as in the case of a vinyl monomer. It thus leads—a priori—to a stable surface/aryl group adduct.

Still, it has been shown, especially in the French patent application FR-A-2 829 046, that the aryl diazonium salts lead to very thin organic films that can grow on themselves: once the grafting on the initial surface has been carried out by electro-cleaving and chemisorption reaction, the film grows by electrical orientation reaction in such a way that a film of polymer conductor but at the cathode. This results in difficulties in carrying out a control of the organic film thicknesses resulting from electrografting of aryl diazonium salts. In summary, the combination in aqueous solution of a diazonium salt and a vinyl monomer can lead to the formation of a grafted film under the condition that the vinyl monomer is soluble in water. However, this method of obtaining grafted films is limited to the rare vinyl monomers that are soluble in water like certain acrylic acids, hydroxylated or aminated vinyls and generally leads to films of poor quality (see article by Bell and Zhang, Journal of Applied Polymer Science, 1999, 73, 2265-272).

The electro-grafting reactions that are currently available according to the prior art thus make it possible to easily obtain a certain variety of organic films on different conductive and semi-conductive substrates using organic solutions. Nevertheless, it will be necessary to extend this range in order to respond to the demands of the industry, to diversify the usage properties of such materials and thus their application possibilities. In addition, the protocols used in industry make use of organic solvents that are notoriously toxic and costly. Thus, it is also desirable to propose new procedures that are less polluting and more profitable for industries.

At the current time, no procedure exists that makes it possible to produce grafted organic films of good quality on electrically conductive or semi-conductive surfaces that can be implemented easily in a protic environment, in particular in aqueous media, using a large variety of polymerizable monomers.

It is in order to solve this technical problem that the inventors have implemented that which is the object of the invention.

SUMMARY OF THE INVENTION

The inventors have discovered, in a surprising and unexpected manner, that it was possible to produce copolymer organic films on an electrically conductive or semi-conductive surface in a protic medium, and especially an aqueous medium, using a large variety of monomers and in particular vinyl monomers, preferably hydrophobic ones.

The inventors have actually implemented a preparation procedure for a copolymer organic film on an electrically conductive or semi-conductive surface by electrolysis of an electrolyte solution comprising the following species: a protic solvent, a primer soluble in the medium, a radically polymerizable monomer, the said procedure being characterized in that the polymerizable monomer is solubilized in micellar form.

Thus the invention has as its first object a procedure for formation of a copolymer organic film on an electrically conductive or semi-conductive surface by electrolysis of an electrolyte solution until the said grafted copolymer organic film is obtained on the said surface, the said procedure being characterized in that:

a) the electrolyte solution contains:
  i) at least one protic solvent,
  ii) at least one primer for radical polymerization, the said primer being soluble in the said protic solvent,
  iii) at least one radically polymerizable monomer,
  iv) at least one surfactant,
b) the electrolysis of the electrolyte solution is carried out with a reducing potential at least equal to the reducing potential of the said primer.

In the sense of the present invention, "copolymer" organic film is understood to mean any polymer film derived from several monomer units of different chemical species and, in particular, any film prepared using at least one type of monomer that is polymerizable, in particular radically, and at least one type of primer, also polymerizable, that is soluble in the protic solvent.

In the sense of the present invention, "primer" is understood as any organic molecule that is able to chemisorb on an electrically conductive or semi-conductive surface by electrochemical reaction and comprises a reactive function with respect to a carbon radical after chemisorption. Thus, for example, the primer can be chosen from among the conjugated systems, the halogen alkanes and the aryl diazonium salts; the polymerizable monomer can be chosen from among the vinyls.

In a non-limiting manner, the electrically conductive or semi-conductive surfaces are chosen from among stainless steel, steel, iron, copper, nickel, cobalt, niobium, aluminum, silver, titanium, silicon with or without its oxide, titanium nitride, tungsten, tungsten nitride, tantalum, tantalum nitride and noble metal surfaces made up of at least one metal chosen from among gold, platinum, iridium and irradiated platinum. According to a preferred embodiment of the invention, the surface used is a surface of steel, in particular stainless steel, for example, stainless steel of the type 316, preferably 316 L.

In the sense of the invention, a primer is considered soluble in a protic solvent if it remains soluble up to a concentration of 0.5 M, i.e. its solubility is at least equal to 0.5 M under normal temperature and pressure conditions. Solubility is defined as an analytical composition of a saturated solution as a function of the proportion of a solute in a given solvent; it can also be expressed in molarity. A solution containing a given concentration of compound will be considered saturated when the concentration is equal to the solubility of the compound in this solvent. Thus, the solubility may be finite just as it may be infinite; in the latter case the compound is soluble in any proportion in the solvent considered.

The protic solvent is advantageously chosen from the group made up of water, acetic acid, hydroxylated solvents like methanol and ethanol, liquid glycols with low molecular weight such as ethylene glycol, and mixtures of them. According to a specific embodiment of the invention, the protic solvent may be used in a mixture with an aprotic solvent, it being understood that the resulting mixture presents the characteristics of a protic solvent. Water is the preferred protic solvent, it is particularly interesting that the water be distilled or deionized.

The primers for radical polymerization according to the invention are aryl diazonium salts.

Among the aryl diazonium salts, the compounds of the following formula (I) can especially be mentioned:

$$R{-}N_2^+, A^- \qquad (I)$$

in which:
A represents a monovalent anion and
R represents an aryl group.

As aryl group of the compounds of formula (I) above, it is especially possible to mention the aromatic or heteroaromatic carbonated structures, possibly monosubstituted or polysubstituted, made up of one or several aromatic or heteroaromatic cycles each comprising three to eight atoms, it being possible for the heteroatom to be N, O, P or S. The substituent or substituents can contain one or several heteroatoms such as N, O, F, Cl, P, Si, Br or S as well as the alkyl groups.

Among the compounds of formula (I) above, A can particularly be chosen from among the inorganic anions such as the halides like $I^-$, $Br^-$ and $Cl^-$, the halogeno boranes such as tetrafluoroborane, and the organic anions such as alcoholates, carboxylates, perchlorates and sulfates.

Among the compounds of formula (I) above, R is preferably chosen from among the aryl groups substituted by the electron attractor groups such as $NO_2$, CO, CN, $CO_2H$, the esters and the halogens. A group R of the aryl type that is especially preferred is the nitrophenyl radical.

By way of compounds of formula (I), it is particularly advantageous to use phenyl diazonium tetrafluoroborate, 4-nitrophenyl diazonium tetrafluoroborate, 4-bromophenyl diazonium tetrafluoroborate, 2-methyl-4-chlorophenyl diazonium chlorate, 4-benzoyl benzene diazonium tetrafluoroborate, 4-cyanophenyl diazonium tetrafluoroborate, 4-carboxyphenyl diazonium tetrafluoroborate, 4-acetamidophenyl diazonium tetrafluoroborate, 4-phenyl acetic acid diazonium tetrafluoroborate, 2-methyl-4-[(2-methylphenyl)diazenyl] benzene diazonium sulfate, 9,10-dioxo-9,10-dihydro-1-anthracene diazonium chloride, 4-nitronaphthalene diazonium tetrafluoroborate and naphthalene diazonium tetrafluoroborate.

The quantity of primer present in the electrolyte solution used according to the procedure of the invention may vary as a function of the experimenter's wishes. This quantity is particularly connected to the thickness of the copolymer organic film desired as well as the quantity of primer that is desirable to be integrated in the film. Thus, in order to obtain a grafted film on the entire surface used, it is necessary to use a minimum quantity of primer that can be estimated by molecular space requirement calculations. According to one specific advantageous embodiment of the invention, the primer concentration in the electrolyte solution is between around $10^{-4}$ and 0.5 M.

The radically polymerizable monomers correspond to monomers that are able to polymerize in radical condition after initiation by a primer. Among these monomers, the vinyl monomers are especially involved, in particular the monomers described in the French patent application FR 05 02516 as well as in the French patent application FR-A-2 860 523, issued under the number FR 03 11491. The monomers that are especially concerned are those which, in contrast to compounds that are soluble in any proportion in the solvent considered, are soluble up to a certain proportion in the solvent, i.e. the value of their solubility in this solvent is finite. According to one preferred embodiment of the invention, the radically polymerizable monomers are thus chosen from among the monomers whose solubility in the protic solvent is finite.

According to an especially advantageous embodiment of the invention, the vinyl monomer or monomers are chosen from among the monomers with the formula (II) below:

(II)

in which the groups $R_1$ to $R_4$, identical or different, represent a non-metallic monovalent atom such as an atom of halogen or an atom of hydrogen or a saturated or unsaturated chemical group such as an alkyl, aryl group, a —$COOR_5$ group in which $R_5$ represents a hydrogen atom or an alkyl group in $C_1$-$C_6$, nitrile, carbonyl, amine or amide.

Among the compounds of formula (II) above, it is possible to mention in particular acrylonitrile, methacrylonitrile, methyl methacrylate, ethyl methacrylate, butyl methacrylate, propyl methacrylate, hydroxyethyl methacrylate, hydroxypropyl methacrylate, glycidyl methacrylate; crotononitrile, pentene nitrile, ethyl crotonate and their derivatives; the acrylamides and especially the aminoethyl, propyl, butyl, pentyl and hexyl methacrylamides, the cyanoacrylates, the di-acrylates and di-methacrylates, the tri-acrylates and tri-methacrylates, the tetra-acrylates and tetra-methacrylates (such as pentaerythritol tetramethacrylate), styrene and its derivatives, parachloro-styrene, pentafluoro-styrene, N-vinyl pyrrolidone, 4-vinyl pyridine, 2-vinyl pyridine, the vinyl, acryloyl or methacryloyl halides, divinylbenzene (DVB), and more generally the vinyl cross-linking agents or those with anacrylate or methacrylate base and their derivatives.

Among the derivatives of crotononitrile, of pentenenitrile and of ethyl crotonate, it is possible to imagine other compounds such as esters, the corresponding acids or the aminated acids connected by their amine function that are easily accessible by simple chemical reactions known to the person skilled in the art.

The preferred monomers according to the invention are those of which the solubility in protic solvent is low. Thus, the monomers that can be used according to the procedure of the invention are preferably chosen from among the compounds of which the solubility in the protic solvent is less than 0.1 M, and most preferably between $10^{-2}$ and $10^{-6}$ M. Among such monomers, it is possible to mention, for example, butylmethacrylate of which the solubility measured under normal temperature and pressure conditions is around $4.10^{-2}$ M. According to the invention, and unless otherwise indicated, the normal pressure and temperature conditions (CNPT) correspond to a temperature of 25° C. and a pressure of $1.10^5$ Pa.

The quantity of polymerizable monomer present in the electrolyte solution can vary as a function of the wishes of the experimenter. This quantity may be greater than the solubility of the monomer considered in the protic solvent used and may represent, e.g. 18 to 40 times the solubility of the said monomer at a given temperature. According to an advantageous embodiment, this concentration is between around 0.1 M and 5 M.

Surfactants are molecules comprising a lipophilic part (apolar) and a hydrophilic part (polar). Among the surfactants that can be used according to the invention, it is possible to mention:

i) anionic surfactants of which the hydrophilic part is negatively charged; they are preferably chosen from among the compounds of formula (III):

(III)

in which:

$R_6$ represents an aryl or alkyl group in $C_1$-$C_{20}$, preferably in $C_1$-$C_{14}$, $A^-$ is an anion chosen from among the sulfonates, the sulfates, the phosphates, the carboxylates, the sulfosuccinates, etc.

$Cat^+$ is a cationic counter-ion, preferably chosen from among the ammonium ion ($NH_4^+$), the quaternary ammoniums such as tetrabutylammonium, and the alkaline cations such as $Na^+$, $Li^+$ and $K^+$;

ii) the cationic surfactants of which the hydrophilic part is positively charged; they are preferably chosen from among the quaternary ammoniums with the following formula (IV):

$$(R_7)_4—N^+, An^- \quad (IV)$$

in which:
the groups $R_7$, identical or different, represent an aliphatic chain, for example, an alkyl chain at $C_1$-$C_{20}$, preferably at $C_1$-$C_{14}$,
$An^-$ is an anionic counter-ion chosen, in particular, from among the derivatives of boron such as tetrafluoroborate or the halide ions such as $F^-$, $Br^-$, $I^-$ or $Cl^-$;
iii) the zwitterionic surfactants which are the neutral compounds having formal electrical charges with one unit and with the opposite sign; they are preferably chosen from among the following compounds of formula (V):

$$Z^-\text{-}R_8\text{-}Z^+ \quad (V)$$

in which:
$R_8$ an alkyl chain at $C_1$-$C_{20}$, preferably at $C_1$-$C_{14}$,
$Z^-$ represents a negatively charged function held by $R_8$, preferably chosen from between sulfate and carboxylate,
$Z^+$ represents a positively charged function, preferably an ammonium;
iv) the amphoteric surfactants that are the compounds that simultaneously behave like an acid or like a base depending on the medium in which they are placed; these compounds may have an zwitterionic nature, the aminated acids are a specific example of this family,
v) the neutral surfactants (non-ionic): the surfactant properties, in particular hydrophilicity, are provided by the functional groups that have no charge such as an alcohol, an ether, an ester or even an amide containing heteroatoms such as nitrogen or oxygen; because of the low hydrophilic contribution of these functions, the non-ionic surfactant compounds are most usually polyfunctional.

The charged surfactants can naturally have several charges.

Among the different meanings of the aryl group of group $R_6$ of the compounds of formula (III) above, it is possible to mention in particular the phenyl cycle, substituted or not, and among the different meanings for the alkyl group $R_6$, the alkyl chains at $C_1$-$C_{20}$ and preferably at $C_1$-$C_{14}$.

As a compound of formula (III), tetraethylammonium para-toluene sulfonate, sodium dodecylsulfate, sodium palmitate, sodium stearate, sodium myristate, di(2-ethylhexyl) sodium sulfosuccinate, methylbenzene sulfonate and ethylbenzene sulfonate are preferably used.

Among the different meanings of the $R_7$ group's quaternary ammoniums of formula (IV) above, it is possible to mention especially the methyl, ethyl, propyl, butyl and tetradecyl groups.

As the compound of formula (IV), ammonium tetradecyl trimethyl bromide (TTAB), alkyl-pyridinium halides having an aliphatic chain at $C_1$-$C_{18}$ and the alkylammonium halides are preferably used.

As the zwitterionic surfactant, it is possible to mention especially N,N-dimethyldocecyl ammonium sodium butanoate, diemethyldodecyl ammonium sodium propanate.

As the amphoteric surfactant, it is possible to mention especially disodium lauroamphodiacetate, the betaines like alkylaminodipropyl betaine or laurylhydroxy sulfobetaine.

As the non-ionic surfactant, it is possible to mention especially the polyethers like the polyethoxylated surfactants such as e.g. polyethylene glycol lauryl ether (POE23 or Brij® 35), the polyols (surfactants derived from sugars), in particular the glucose alkylates such as e.g., glucose hexanate.

Surfactants that can be used according to the invention are also emulsifiers, i.e., when they are present in small quantities, they facilitate the formation of an emulsion or increase the colloidal stability by decreasing the speed of aggregation or the speed of coalescence or both. Measurements of one or the other of the speeds according to techniques known by a person skilled in the art like the measurement of the size of drops by diffusion of light can make it possible to determine the best emulsifier from among the recommended surfactants in each of the cases.

Among the surfactants preferred according to the invention, it is possible to mention the anionic surfactants such as the sulfonates, the quaternary ammoniums and the non-ionic surfactants like the polyoxyethylenes.

The quantity of surfactants that may be present in the electrolyte solution is variable, in particular it must be adequate to allow the formation of the copolymer organic film; the minimum quantity of surfactant can easily be determined by sampling the electrolyte solutions of identical composition but with variable concentration of surfactant. In a general manner, the concentration of surfactant is such that the critical micellar concentration (CMC) will be achieved and thus there will be the formation of micelles. The CMC of a surfactant can be determined by the methods known to the person skilled in the art, for example, by measurements of surface tensions.

The concentration of surfactant within the electrolyte solution is typically at least equal to the CMC and generally between 0.5 mM and 5 M, and preferably between around 0.1 mM and 150 mM. The recommended concentration of surfactant is usually 10 mM.

The interest in the surfactant is based on its capacity to form micelles in a solvent that promotes the growth of macroradicals by isolating them from the external medium, thus ensuring the growth of the film.

Advantageously, the pH of the electrolyte solution is less than 7, and typically less than or equal to 2. It is recommended that work be carried out at a pH between 1.6 and 2.2 when the primer is a diazonium salt. If necessary, the pH of the electrolyte solution can be adjusted to the desired value using one or several acidifying agents that are well known to the person skilled in the art, for example, using mineral or organic acids such as hydrochloric acid, sulfuric acid, etc.

The presence of protons in the medium especially facilitates the formation of the hydrogen radicals.

The electrolysis of the electrolyte solution is preferably carried out under agitation, e.g., with mechanical agitation and typically using a magnetic bar or in some cases by bubbling gas through.

It is also preferable that the procedure comprises an additional step, prior to the electrolysis step, of cleaning the surface on which the copolymer organic film will be formed, in particular by sanding and/or polishing; a supplementary treatment using ultrasound with an organic solvent like methanol is also recommended. It is also advantageous if the protic solvent is degassed before use or purged using an inert gas like argon.

The potential applied to the electrolyte solution must correspond at least to that of the primer in order to permit electrolysis that corresponds to the initiation of polymerization. It may be greater than that of the protic solvent; as well as if the protic solvent contains an elevated number of protons and there will be a formation of hydrogen radicals in the medium which will facilitate the formation of the film by activation of the micelles formed.

According to a first advantageous embodiment of the invention, the electrolyte solution contains at least one surfactant, present with acid pH, and a potential applied that is adequate to cause the formation of the hydrogen radicals (i.e., at least more cathodic than −0.8 V). In this case, it is not necessary for the electrolyte solution to contain a significant proportion of primer, the theoretical adequate quantity corresponds to that necessary to form an organic film, called "primary film," obtained by grafting of the primer over the entire surface. In the case where the primer is a diazonium salt, a sweeping of the potential will involve a reduction of the diazonium with formation of a polynitrophenylene sub-layer, then reduction of the $H^+$ with massive formation of hydrogen radicals which prime the radical polymerization in the micelles. It is recommended that the current applied be on the order of $mA.cm^{-2}$, the working current density preferably being less than or equal to $10^{-4}$ $A.cm^{-2}$. An optimum value can be estimated using the average number of grafting sites on the surface considered.

According to another advantageous embodiment of the invention, the concentration of primer is essentially increased, for example, it is $10^{-2}$ M, in such a way that it can simultaneously serve as a primer within the micelles and for primary adhesion on the surface. In this case, it is preferable that the working potential used will be at maximum greater than 5% of the potential value of reduction of the primer considered that is present within the electrolyte solution and no more cathodic than −0.8 V. In fact, in order to promote the surface reaction, it is advantageous to place it at a value close to the reducing threshold of the compound that will react on the surface.

The electrolysis of the electrolyte solution can be carried out independently by polarization under linear or cyclic voltamperometry conditions, under potentiostatic, potentiodynamic, intensiostatic, galvanostatic, galvanodynamic or under chronoamperometry conditions, single or pulsed. Advantageously, it is carried out by polarization under cyclic voltamperometry conditions. In this case, the number of cycles will preferably be between 1 and 100 and even more preferably between 1 and 10.

The thickness of the copolymer organic film formed on the electrically conductive or semi-conductive surface is controlled by simple variation of the experimental parameters that are accessible in an empirical manner to the person skilled in the art according to the polymerizable monomer and the primer that are used. Thus, in a non-exhaustive manner, the film thickness can be controlled by the number of sweeps in the case of a cyclic voltamperometry. It can also be controlled by the initial concentration of electroactive species, the maximum potential value imposed and the polarizing time, it being possible for the latter to vary either directly, i.e. the time of an electrolysis, or by the bias of a sweeping speed in voltamperometry.

The procedure conforming to the invention can thus be carried out in particular in an electrolysis cell comprising three electrodes: a first working electrode making up the surface intended to receive the film, a counter-electrode as well as a reference electrode.

The present invention also has as its object electrically conductive or semi-conductive surfaces obtained by implementing the procedure described above, the said surfaces being characterized by the fact that they comprise at least one face that is at least partially covered by a copolymer organic film grafted with at least one radically polymerizable monomer and with at least one radical primer, the said primer being soluble in the electrolyte solution used in the course of the said procedure.

The copolymer organic films obtained according to the invention advantageously have a thickness between 5 and 1000 nm, inclusive, and even more preferably between 10 and 200 nm, inclusive.

The surfaces obtained according to the invention can be used in any type of industry and in particular in the electronics and microelectronics industries (for example, for the preparation of microelectronic components), for the preparation of biomedical devices such as e.g. devices that are implantable in the organism (for example, stents), screening kits, etc.

The electrolyte solutions used according to the invention are novel and, because of this, make up another object of the invention.

The present invention thus has as an object an electrolyte solution characterized in that it includes:
i) at least one protic solvent,
ii) at least one primer for radical polymerization, the said primer being soluble in the said protic solvent,
iii) at least one radically polymerizable monomer, and
iv) at least one surfactant.

Electrolyte solutions containing at least one surfactant of formulas (II), (IV) or (V) such as defined above are preferred according to the invention.

Among such solutions, the especially preferred electrolyte solutions are chosen from among those including:
i) a protic solvent chosen from among water, ethylene glycol, ethanol, acetic acid and mixtures of them;
ii) at least one soluble primer chosen from among the aryl diazonium salts,
iii) at least one polymerizable monomer chosen from among the vinyl monomers with finite solubility in the said protic solvent, and
iv) at least one surfactant of the formula (III), (IV) or (IV) such as defined above.

Finally, the present invention has as its object the use of at least one electrolyte solution such as defined above for producing copolymer organic films grafted on electrically conductive or semi-conductive surfaces.

BRIEF DESCRIPTION OF THE DRAWINGS

In addition to the preceding provisions, the invention also comprises other provisions that result from the description to follow, which refers to the examples of the formation of copolymer organic films on steel surfaces according to the procedure of the invention as well as to FIGS. 1 to 12 that are attached, which include:

FIG. 1 represents the electrolysis cell used in Example 1 above. This electrolysis cell is made up of an electrolysis tank 1 filled with an electrolyte solution 2 in which three electrodes are arranged: one stainless steel working electrode 3, a counter-electrode 4 made up of a plate of carbon and a reference electrode 5 which is a saturated calomel electrode (SCE). The three electrodes are connected to a potentiometer 6;

It must be understood that all of these examples are given only for illustration of the invention and they do not in any way constitute any limitations whatsoever.

EXAMPLES

The examples presented above were carried out on the surfaces made up of stainless steel plates of around 6 cm².

Example 1

Figure 1:
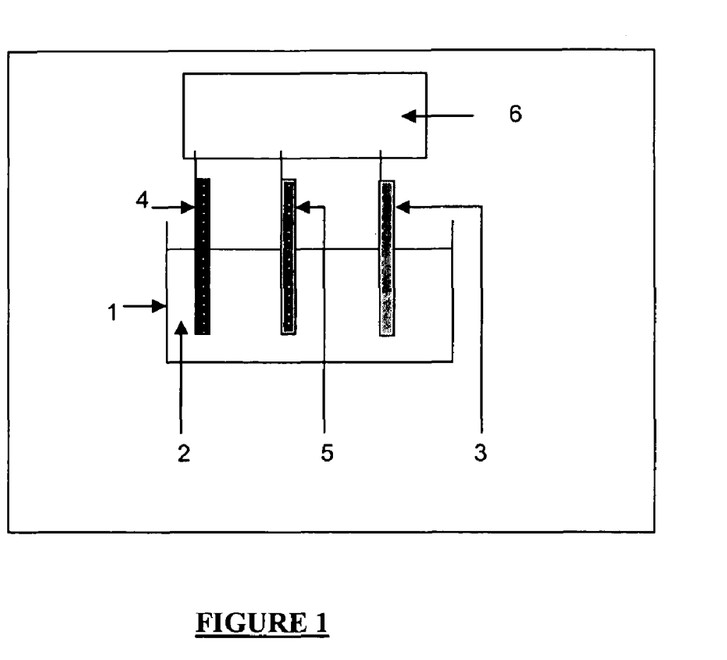

Synthesis in Water of a Thin Film of Polyacrylonitrile Grafted on a Surface of Stainless Steel In this example and the following, the electrolysis was carried out according to the assembly shown in FIG. 1, in a Teflon container 1 filled with an electrolyte solution 2 and comprising three electrodes. A reference electrode 5 that is an electrode of saturated calomel (SCA), a counter-electrode 4 of platinum and a working electrode 3 of stainless steel as indicated above. The electrodes have been coupled to a EG & G 273A brand potentiometer 6 sold by the PAR company (Princetown Applied Research).

In this example, the following electrolyte solution was prepared:

The protic solvent is deionized water containing 5 mol.l⁻¹ (a) acrylonitrile (of which the solubility in deionized water is around 1 mol.l⁻¹), 1.45 mol.l⁻¹, (b) paratoluene sulfonate tetraethylammonium (anionic surfactant) and 1.8 10⁻³ mol.l⁻¹ and (c) 4-nitrophenyl diazonium tetrafluoroborate (primer). The pH of the solution was adjusted to 2 by addition of a sulfuric acid solution. The molecules (a), (b) and (c) that were used are represented below:

Several hours before their use, the plates of steel (working electrodes) were sanded with 10 μm sandpaper, then polished using a solution of diamond powder with granulometry of 2 μm.

The plates were then treated for five minutes using ultrasound in ethanol, then acetone.

The electrolyte solution was placed in the electrolysis cell with three electrodes. The electrolyte solution was agitated by a magnetic agitator (not shown in FIG. 1), the polarization of the electrode being implemented by cyclic voltametry, 10 cycles were carried out at a sweeping speed of 10 mV/s between the equilibrium potential of this system near 0 V and −1.1 V.

Figure 2:
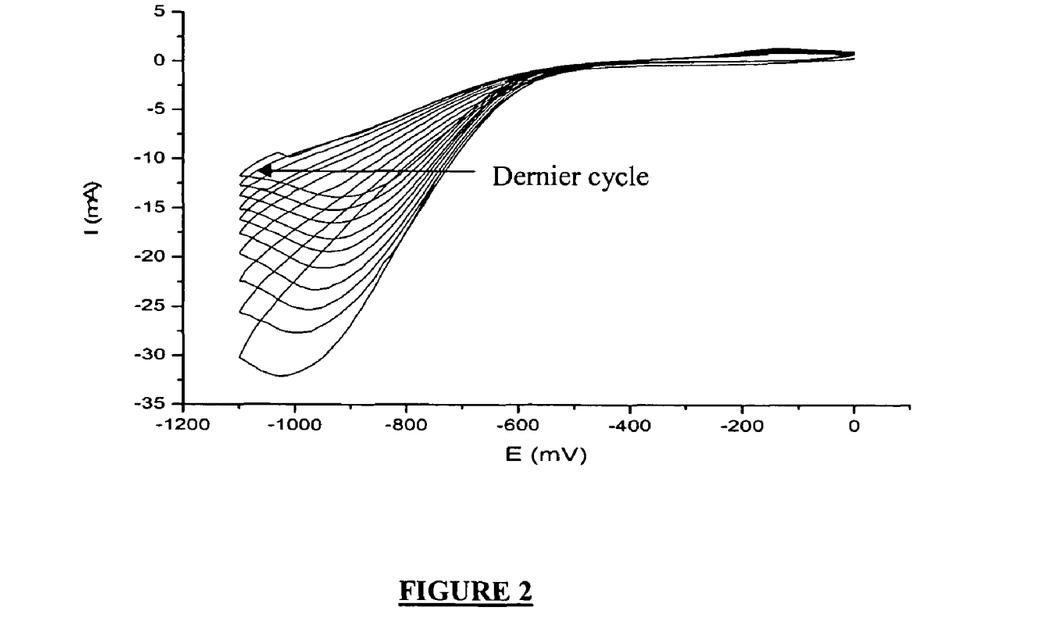
FIG. 2 represents the voltammogram (cyclic voltametry; 10 cycles) recorded using an aqueous solution of acrylonitrile (5 M), of paratoluene sulfonate tetraethylammonium (1.46 M), and 4-nitrophenyl diazonium tetrafluoroborate (0.0018 M), pH=2.02, agitation, stainless steel working electrode, sweeping speed of 10 mV/s.

The voltammogram obtained is shown in FIG. 2, attached.

Mainly the trend in reduction of protons is observed (which starts at around −0.6 V), which masks the reduction of the cation of the diazonium salt (generally located near −0.2 V), followed by a reduction peak centered around −1 V with the first sweeping. These peaks and their trends are characteristic of a passivation phenomenon of the electrode during its progressive covering by a polymer film. This film is actually little soluble in the electrolyte and thus represents a barrier to the redox reactions. This is translated into a lowering of current in the electrolysis cell.

The modified surfaces are then plunged into dimethylformamide (DMF) with ultrasound for three minutes. DMF is claimed to be one of the best solvents of polyacrylonitrile (PAN). By this treatment, any polymer that may not be grafted to the surface of the metal is eliminated. The surfaces are then plunged into a mixture 50:50 (v/v) water/ethanol with agitation in order to eliminate any possible traces of DMF and finally rinsed with acetone.

The samples thus treated are then analyzed using infrared spectroscopy in order to determine the molecular structure. The infrared spectrum obtained is presented in FIG. 3, attached.

Figure 3:
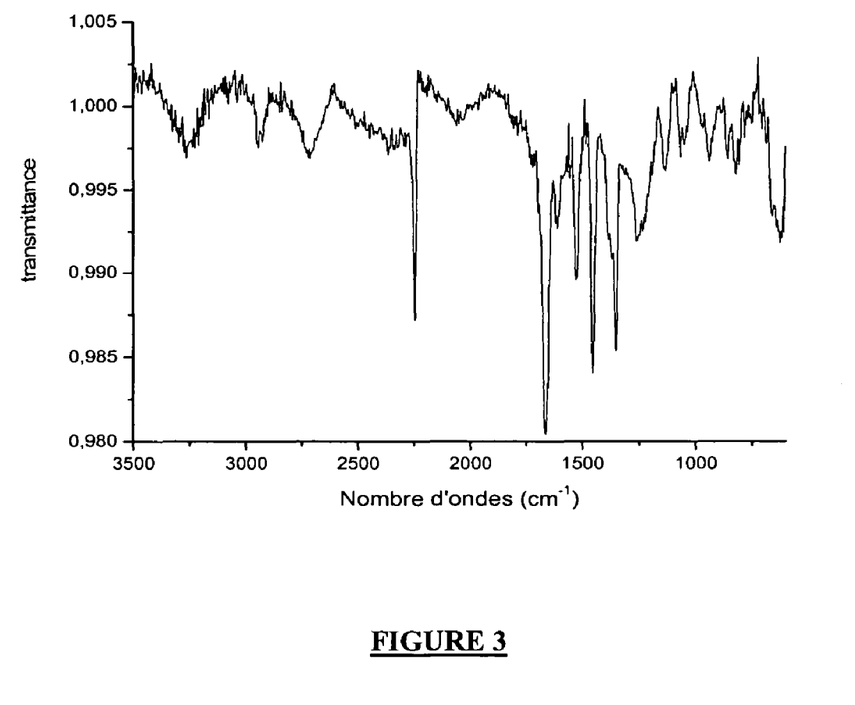
FIG. 3 represents the infrared spectrum (transmittance (%) as a function of the wave number in $cm^{-1}$) of the copolymer organic film obtained using the electrolyte solution described above for FIG. 2 after rinsing with a water/ethanol solution (50:50 v/v), then acetone.

On this spectrum, absorption bands are found that are characteristic of polyacrylonitrile (PAN) and in particular the characteristic band of the nitrile group near 2240 cm$^{-1}$. Its intensity is close to 1.5% of the transmittance, which equals a thickness of around 50 nanometers. The absorption bands of the polynitrophenylene are also visible at 1530 and 1350 cm$^{-1}$.

Taking into account the relative intensities of the absorption bands of the two polymers, it is possible to estimate that this copolymer film comprises one tenth of the polynitrophenylene (the equivalent of a thickness of around 5 nm) for nine tenths of the PAN (around 50 nm). This estimation is based on samples of pure polynitrophenylene and PAN, prepared independently and characterized by IR and profilometry.

Figure 4:
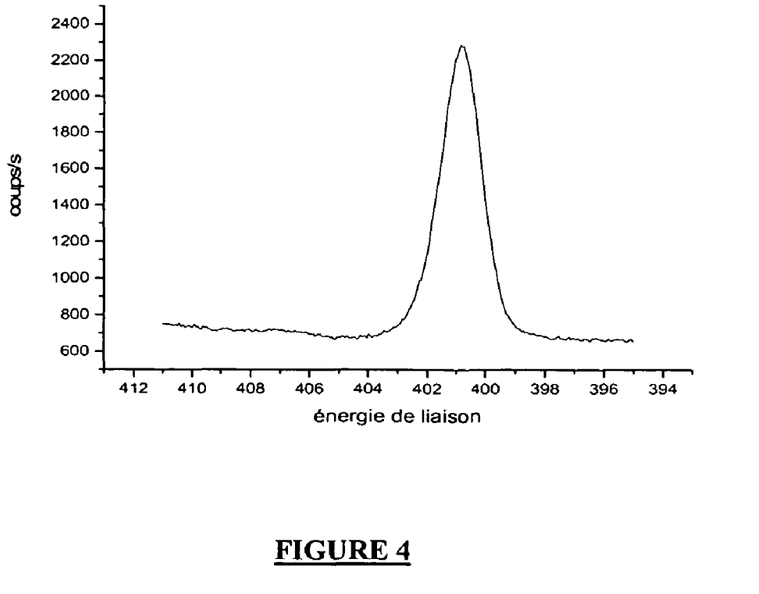
FIG. 4 represents the spectrum N is in x-ray photoelectron spectroscopy (XPS) of the copolymer organic film obtained using the electrolyte solution described above for FIG. 2.

An analysis by ESCA spectrometry (*Electron Spectrometry for Chemical Analysis*—this involves the techniques called XPS: photoelectron spectroscopy with x-rays) was also carried out on this sample. This made it possible to verify that the external layer of the polymer grafted on the metal surface corresponds well to the polyvinyl, in this case PAN. In fact, this technique is not sensitive to any more than the 15 last nanometers of the sample, yet the XPS marker of polynitrophenylene, the NO$_2$ group, is not found in this zone. In fact, this presents a peak N 1 s centered at 407 eV while the peak N 1 s of a nitrile group is centered at 400 eV. FIG. 4 that is attached shows the spectrum N 1 s of the previous sample.

The mechanism proposed for formation of the film is connected with passage of the current which produces radicals using the diazonium salt according to DIAGRAM B below:

DIAGRAM B

The radical formed grafts onto the metal (working electrode) according to DIAGRAM C below:

DIAGRAM C

-continued

Figure 5:
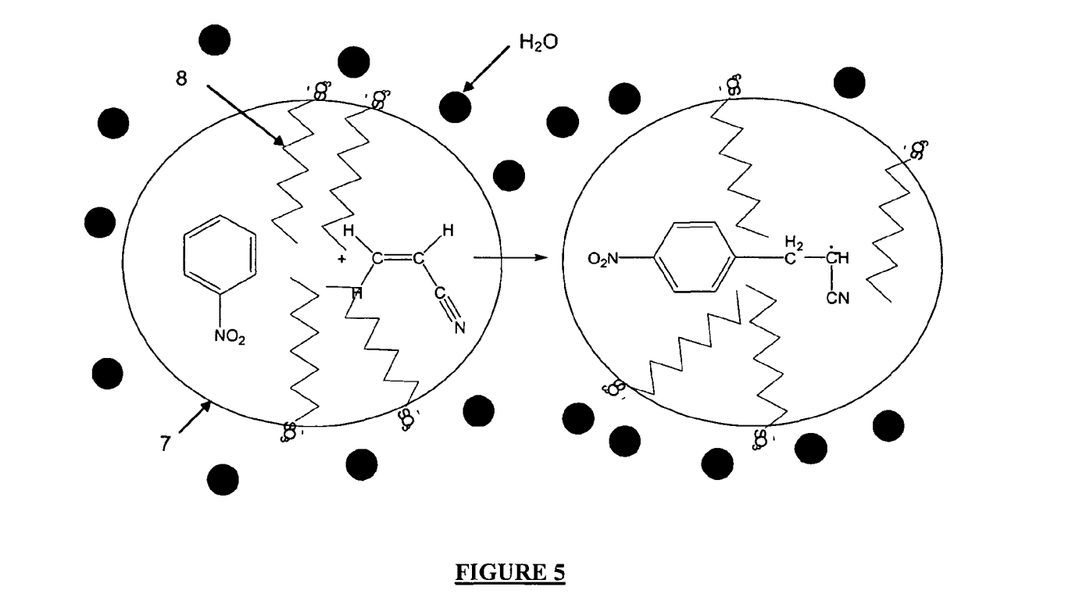
FIG. 5 represents DIAGRAM E of a micellar radical polymerization (micelles 7) of the acrylonitrile in the presence of paratoluene sulfonate tetraethylammonium (surfactant 8) and 4-nitrophenyl diazonium tetrafluoroborate in aqueous solution holding the macroradicals.

The excess of nitrophenyl radicals may:
either participate in thickening the grafted layer according to the mechanism shown in Diagram D below:

DIAGRAM D or integrate a micelle 7 of monomer and prime the radical polymerization reaction to lead to macroradicals according to DIAGRAM E shown in FIG. 5 attached.

In the case of an acid medium, passage of the current can also form hydrogen radicals according to the following reactions:

$$H^{\oplus} + e^- \rightarrow H^{\bullet}$$

An equilibrium still exists between the species; the formation of hydrogen radicals, even though it is of less importance, is observed at less acid pH values; the same mechanism may apply here.

Part of the radicals dimerize and yield gaseous hydrogen:

The other part, like the nitrophenyl radicals, can prime the polymerization in the acrylonitrile micelles according to the reaction shown in DIAGRAM F below:

DIAGRAM F

Macroradicals in the micelles are thus obtained according to the reaction shown in DIAGRAM G below:

DIAGRAM G

A termination reaction according to DIAGRAM H below may take place in the micelle; the polymer will then remain in solution:

DIAGRAM H

These macroradicals may also react on the polynitrophenylene grafted on the electrode surface to form a film according to DIAGRAM I below:

According to Hammet's Law, the radical attacks an ortho of the $NO_2$ group monomeric attractor, then it results in a repeat aromatizing of the cycle with six carbon atoms due to the loss of a hydrogen radical according to the reaction shown in DIAGRAM J below:

DIAGRAM J

Example 2

Grafting of a Polybutyl Methacrylate (PBuMA) Film on a Stainless Steel Surface by Electro-Polymerization in emulsion (Anionic Surfactant)

The surfaces were previously sanded with 10 μm sandpaper, then with a solution of diamond powder with a granulometry of 3 μm. The surfaces were then treated for five minutes with ultrasound in ethanol and then in acetone.

The reaction medium was made up of an aqueous electrolyte solution of butyl methacrylate (BuMA, solubility<0.1 mol.l$^{-1}$ in water) at 0.69 mol.l$^{-1}$, of sodium dodecylsulfate (SDS) at 8 mmole.l$^{-1}$ and 4-nitrobenzene diazonium tetrafluoroborate at 2 mmol.l$^{-1}$. The pH solution was adjusted to 1.70 by the addition of pure sulfuric acid. The agitation was

DIAGRAM I maintained by bubbling argon through the solution at the time of electrolysis. The molecules used in this example are represented in the following:

BuMA: $H_2C=C(CH_3)-C(=O)-OC_4H_9$

SDS: $CH_3(CH_2)_{11}-O-SO_3^-; Na^+$ 4-nitrobenzene diazonium tetrafluoroborate: $N\equiv N^+-C_6H_4-NO_2, BF_4^-$ The electrochemical parameters chosen here were: two cycles at equilibrium at −1.1 V at a speed of 10 mV/s with agitation by bubbling argon.

Figure 6:
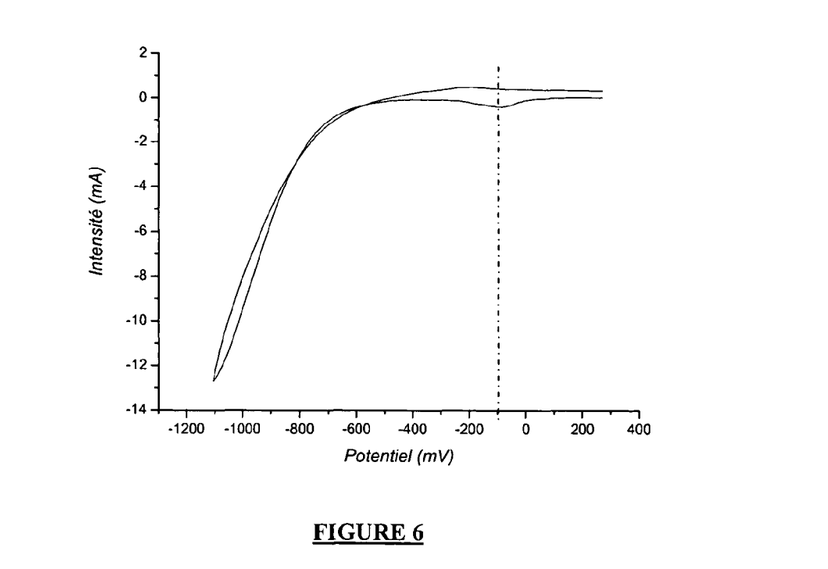
FIG. 6 represents the voltammogram (cyclic voltametry: first cycle) recorded using an aqueous solution containing butylmethacrylate (BuMA) 0.69 M, sodium dodecylsulfate 8 mM, and 4-nitrobenzene diazonium tetrafluoroborate 2 mM, pH=1.70, agitation by bubbling in argon, stainless steel working electrode, sweeping speed 10 mV/s.

The voltammogram obtained is shown in FIG. 6, attached.

On this voltammogram, the reduction of the diazonium cation can be distinguished near −0.1 V/SCE, followed by the reduction trend of the protons that starts near −0.6 V/SCE.

Figure 7:
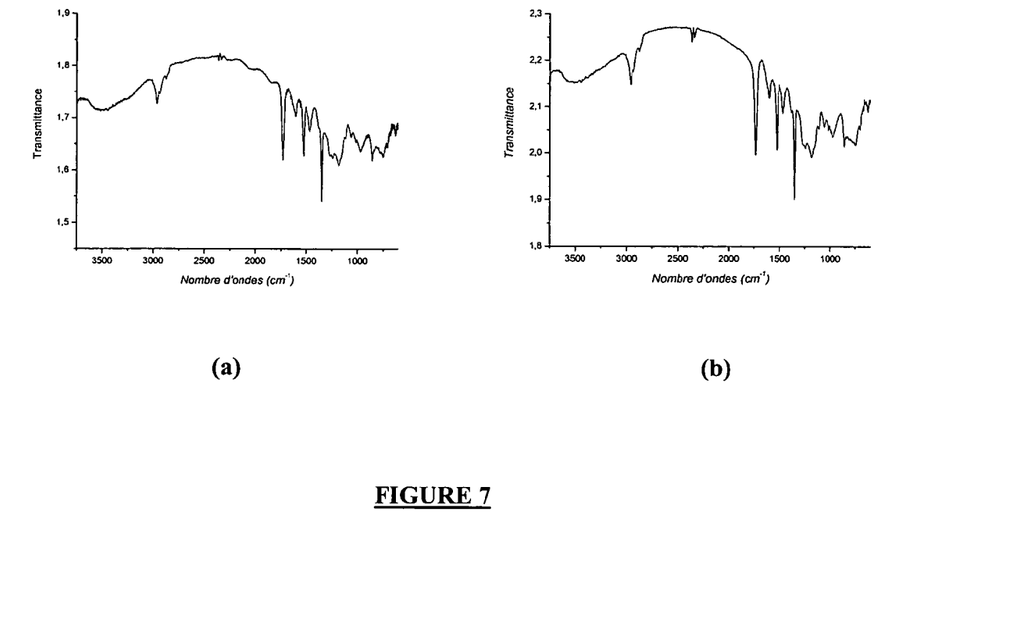
FIG. 7 represents the infrared spectrum (transmittance (%) as a function of the wave number in $cm^{-1}$) of the organic copolymer film obtained using the electrolyte solution described above for FIG. 6 before (7a) and after (7b) rinsing with dimethylformamide with ultrasound for three minutes.

The sample was then subjected to rinsing with DMF with ultrasound for 3 minutes and finally was analyzed using infrared spectroscopy. The IR spectra thus obtained (before rinsing (7a): carbonyl bond: 13% transmittance and after rinsing (7b): carbonyl bond: 12.5% transmittance) are shown in FIG. 7 attached.

The band at 1740 cm$^{-1}$ corresponds to the CO carbonyl groups CO with the ester function COOC$_4$H$_9$.

Thus there is a polyBuMa grafted on the surface of the electrode. Its transmittance is around 13%, which corresponds to a film thickness of around 100 nanometers.

The presence of bands at 1530 cm$^{-1}$ and 1350 cm$^{-1}$ is noted, which correspond to NO$_2$ groups. The band at 1600 cm$^{-1}$ corresponds to double bonds of benzene.

The spectrum of a poly (nitrophenylene block BuMA) copolymer is thus recognized.

Taking into account the relative intensities of the absorption bands of the two polymers, it is possible to estimate that the layer grafted is composed of around 15 nm of polynitrophenylene (grafted on the metal) and around 100 nm of PAA grafted on the latter (global thickness 115 nm).

An ESCA (XPS) analysis has also been carried out on this sample (not shown); this makes it possible to verify that the external layer of the polymer grafted on the surface of the metal corresponds well to the polyvinyl, in this case the polyBuMA. In fact, this technique is not sensitive except up to the 15 last nanometers of the sample, still the XPS marker of nitrogen is not found in this zone. This makes it possible to confirm that the external layer of the sample contains nothing but polyBuMA.

The same experiments have been carried out without adding the primer, i.e. the diazonium salt in an electrolyte solution.

Figure 8:
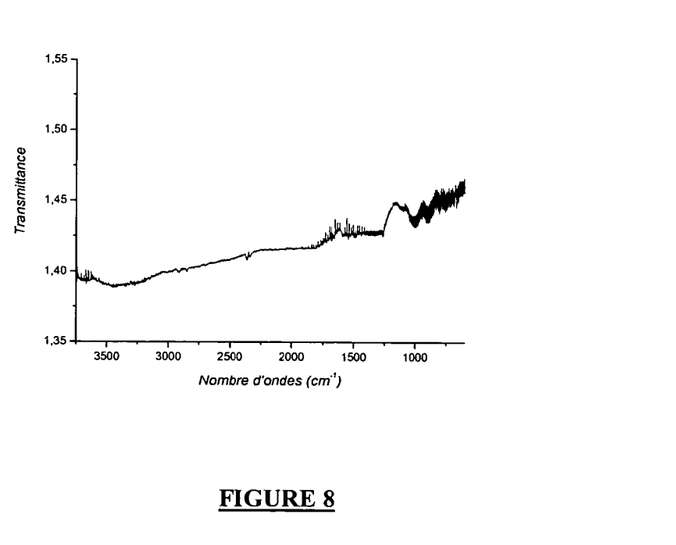
FIG. 8 represents the infrared spectrum (transmittance (%) as a function of the wave number in $cm^{-1}$) of a working electrode subjected to the same conditions as those given for FIG. 6 but using an aqueous electrolyte solution that is not a part of the invention (without primer) containing only butylmethacrylate (BuMA) 0.69 M and sodium dodecylsulfate 8 mM.

The infrared spectrum of the film obtained under these conditions is shown in FIG. 8 attached.

It can be seen that under these conditions, the polymer film is not constructed (absence of the capturing sub-layer). This experiment validates the general mechanism of construction of the grafted layers.

An XPS analysis was also carried out (not shown). The absence of the nitrogen level 1 s makes it possible to confirm that the external layer of the sample (at least the last 15 nanometers) contains only pBuMA.

These two first examples make it possible to show that the procedure according to the invention makes possible the use of monomers with very different solubilities in water to form organic films grafted on stainless steel substrates.

The two examples below are devoted to the influence of the surfactant nature and make it possible to conclude that different families of surfactants allow the formation of polymer films in water as described above.

Example 3

Grafting of a Film of Polybutyl Methacrylate (PBuMA) on a Stainless Steel Surface by Electro-Polymerization in Emulsion (Cationic Surfactant)

The electrolysis was carried out in a Teflon cell with three electrodes. The reference electrode is an SCE, the counter-electrode is a plate of carbon and the working electrode is stainless steel (316 L). The electrodes were coupled to a potentiometer of the EG & G 273A brand.

The surfaces were previously sanded with 10 μm sandpaper, then with a diamond powder with a granulometry of 3 μm. The surfaces were then treated for five minutes with ultrasound in ethanol, then in acetone.

The reaction medium was composed of an electrolytic aqueous solution containing butyl methacrylate at 0.69 mol.l$^{-1}$, of ammonium tetradecyl trimethyl bromide (TTAB) at 8 mmole.l$^{-1}$ and 4-nitrobenzene diazonium tetrafluoroborate at 4 mmole.l$^{-1}$. The pH of the solution was adjusted to 1.7 by the addition of pure sulfuric acid. Agitation was maintained by bubbling argon into the solution at the time of electrolysis.

The electrochemical parameters chosen here were: five cycles with equilibrium potential at −1.1 V with a speed of 10 mV/s, then agitation by bubbling of argon.

Figure 9:
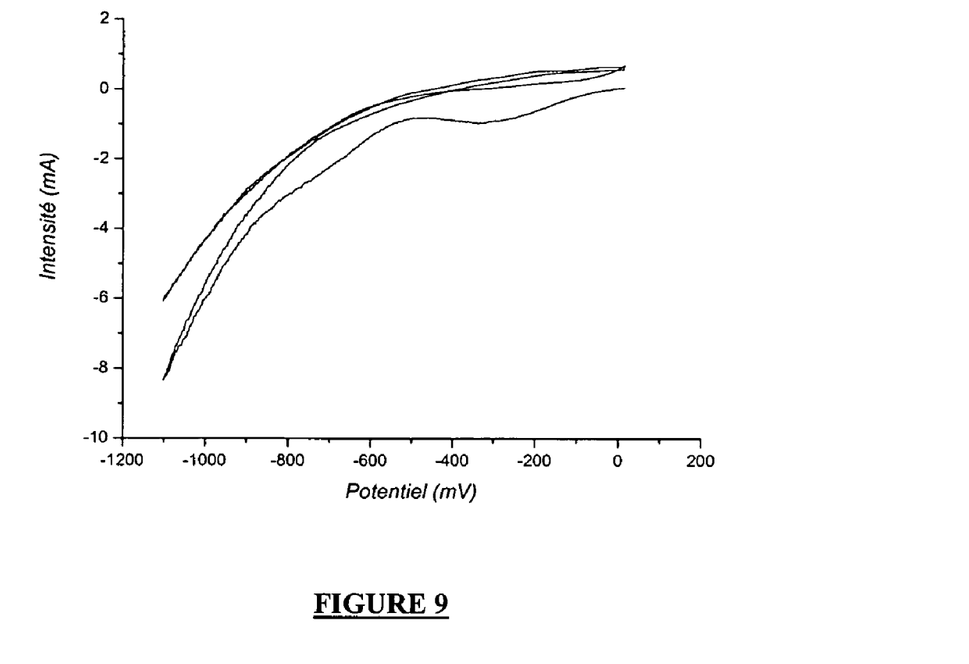
FIG. 9 represents the voltammogram (cyclic voltametry: first and last cycles) recorded using an aqueous electrolyte solution containing 0.69 M of BuMA, 8 mM of ammonium tetradecyl trimethyl bromide, and 2 mM of de 4-nitrobenzene diazonium tetrafluoroborate, pH=1.70, with agitation using argon bubbling, working electrode of stainless steel, sweeping speed of 10 mV/s.

The voltammogram obtained is shown in FIG. 9, attached.

On this voltammogram, it is possible to distinguish the reduction of the diazonium cation around −0.3 V/SCE, followed by a reduction trend of the protons which starts at around −0.5 V/SCE.

Figure 10:
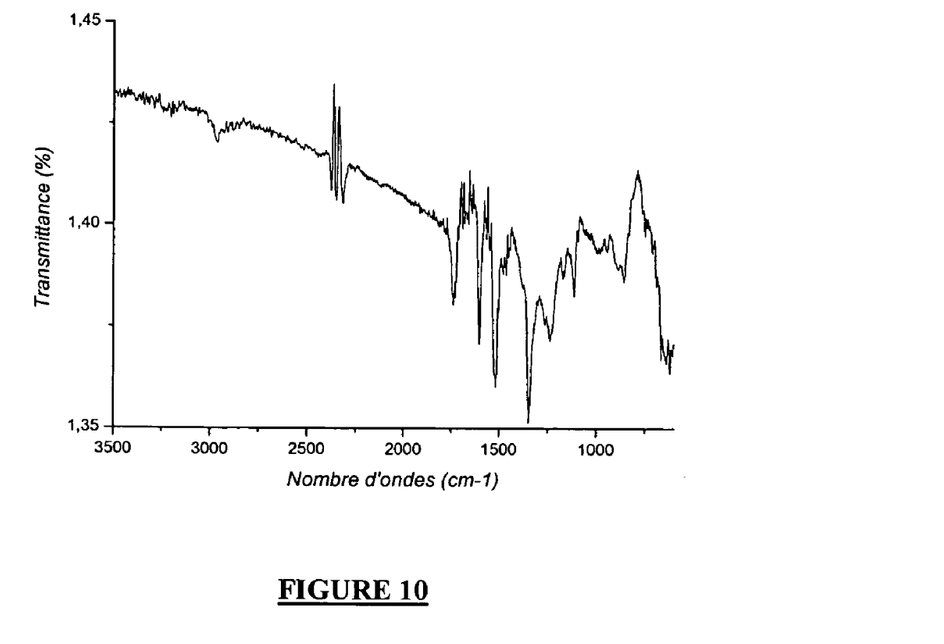
FIG. 10 represents the infrared spectrum (transmittance (%) as a function of the wave number in $cm^{-1}$) by reflection (IRRAS) of the organic copolymer film obtained using the electrolyte solution described above for FIG. 9 after rinsing with a water/ethanol solution (50:50 v/v), then acetone.

The sample was then subjected to the same rinsing treatment as that described above in Example 1 and was finally analyzed using infrared reflection spectroscopy (IRRAS). The IRRAS infrared spectrum of the film obtained under these conditions is shown in FIG. 10, attached.

The band at 1740 cm$^{-1}$ corresponds to the carbonyl CO groups of the function ester COOC$_4$H$_9$.

Thus, there is truly a polyBuMA grafted on the surface of the electrode. Its transmittance is close to 2%, which corresponds to a thickness of the PBuMA of around 20 nanometers.

The presence of bands at 1530 cm$^{-1}$ and 1350 cm$^{-1}$ (around 3% transmittance) can be noted which correspond to NO$_2$ groups.

The band at 1600 cm$^{-1}$ corresponds to double bonds of benzene.

Thus, it is possible to recognize the spectrum of a poly (nitrophenylene BuMA) copolymer.

Taking into account the relative intensities of the absorption bands of the two polymers, it is possible to estimate that the grafted layer is made up of around 5 nm of polynitrophenylene (grafted on the metal) and around 20 nm of PBuMA grafted on the latter.

The small thickness of this sample may explain the absence of passivation peak confirmed on the voltammograms. Only an improvement in reduction is observed at the first sweeping around −0.8 V (see FIG. 9, attached).

Example 4

Grafting of a Film of Polybutyl Methacrylate (PBuMA) on a Stainless Steel Surface by Electro-Polymerization in Emulsion (Neutral Surfactant)

The electrolysis was carried out in a Teflon cell with three electrodes. The reference electrode is an SCE, the counter-electrode is a sheet of carbon and the working electrode is of stainless steel (316 L). The electrodes were coupled with a potentiometer of the EG & G 273A brand.

The surfaces were previously sanded with 10 µm sandpaper, then with a solution of diamond powder with a granulometry of 3 µm. The surfaces were then treated for five minutes with ultrasound in ethanol, then in acetone.

The reaction medium was made up of an electrolytic aqueous solution of butyl methacrylate at 0.69 mol.l$^{-1}$, of polyethylene glycol lauryl ether (Brij® 35 sold by the Aldrich company) at 8 mmole.l$^{-1}$ and 4-nitrobenzene diazonium tetrafluoroborate at 4 mmole.l$^{-1}$. The pH of the solution was adjusted to 1.7 by the addition of pure sulfuric acid. Agitation was maintained by bubbling argon into the solution at the time of electrolysis.

The Brij® 35 used in this example has the following structure:

$$CH_3-(CH_2)_{11}-O-(CH_2-CH_2-O)_{23}-H$$

The electrochemical parameters chosen here were: one cycle with equilibrium potential at −1.1 V at a speed of 10 mV/s with agitation by argon bubbling.

Figure 11:
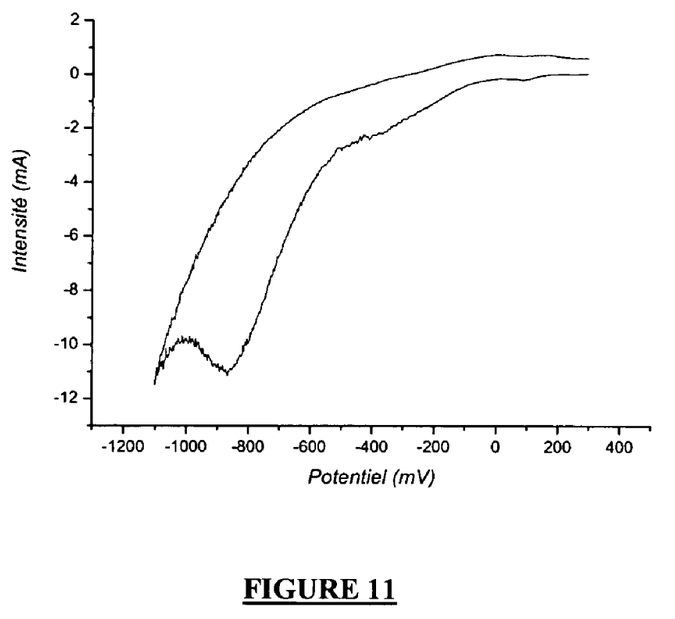
FIG. 11 represents the voltammogram (cyclic voltametry: a single cycle) recorded using an aqueous electrolyte solution containing 0.69 M butyl methacrylate, 8 mM of Brij® 35, and 2 mM 4-nitrobenzene diazonium tetrafluoroborate, pH=1.70, with agitation by bubbling of argon, stainless steel working electrode, sweeping speed of 10 mV/s.

The voltammogram of the film thus obtained is shown in FIG. 11, attached.

On this voltammogram, it is possible to distinguish the reduction of the diazonium cation at around −0.3 V/SCE, followed by a trend of reduction in protons that starts at around −0.6 V/SCE.

It is also possible to observe a reduction peak centered at around −0.85 V. This peak is characteristic of a passivation phenomenon of the electrode by its covering with a film of polymer. This film, which is little soluble in the electrolyte, thus represents a barrier to redox reactions, which translates into a lowering of the current in the electrolysis cell.

Figure 12:
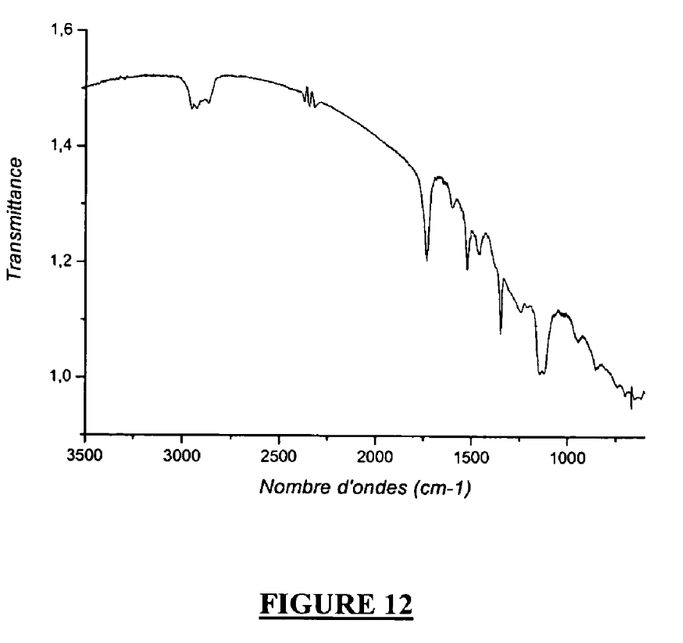
FIG. 12 represents the infrared spectrum (transmittance (%) as a function of the wave number in $cm^{-1}$) by reflection (IRRAS) of the organic copolymer film obtained using the electrolyte solution described above for FIG. 11 after rinsing with a water/ethanol solution (50:50 v/v), then acetone.

The sample was then subjected to the same rinsing treatment as that described above for Example 1 and was finally analyzed using IRRAS. The infrared IRRAS spectrum of the film obtained under these conditions is shown in FIG. 12, attached.

The band at 1740 cm$^{-1}$ corresponds to the carbonyl CO groups of the function ester COOC$_4$H$_9$.

There is thus a polyBuMA grafted on the surface of the electrode. Its transmittance is near 15%, which corresponds to a thickness of PBuMA of around 120 nanometers.

The presence of bands at 1530 cm$^{-1}$ and 1350 cm$^{-1}$ (around 10% of transmittance) can be noted, which corresponds to NO$_2$ groups.

The band at 1600 cm$^{-1}$ corresponds to double bonds of benzene.

Thus, it is possible to recognize the spectrum of a poly (nitrophenylene BuMA) copolymer.

Taking into account the relative intensities of the absorption bands of the two polymers, it is possible to estimate that the grafted layer is made up of around 15 nm polynitrophenylene (grafted on the metal) and around 120 nm of PBuMA grafted on the latter.

The invention claimed is:

1. Method for forming a copolymer organic film on an electrically conductive or semi-conductive surface by electrolysis of an electrolyte solution until the said copolymer organic film is grafted on the said surface, the said method being characterized in that:
    a) the electrolyte solution contains:
        i) at least one protic solvent,
        ii) at least one aryl diazonium salt as primer for radical polymerization, the said aryl diazonium salt being soluble in the said protic solvent,
        iii) at least one radically polymerizable monomer having a solubility in the protic solvent lower than 0.1 M, and
        iv) at least one non-ionic surfactant selected from the group consisting of polyethoxylated surfactants and polyols,
    b) the electrolysis of the electrolyte solution is carried out with a reducing potential at least equal to the reducing potential of the said primer, and the working potential being at maximum greater than 5% of the potential value of reduction of the primer and no more cathodic than −0.8 V.

2. Method according to claim 1, characterized in that the electrically conductive or semi-conductive surface is selected from the group consisting of stainless steel, steel, iron, copper, nickel, cobalt, niobium, aluminum, silver, titanium, silicon with or without its oxide, titanium nitride, tungsten, tungsten nitride, tantalum, tantalum nitride and noble metal surfaces made up of at least one metal selected from the group consisting of gold, platinum, iridium and irradiated platinum.

3. Method according to claim 1 or 2, characterized in that the protic solvent is selected from the group consisting of water, acetic acid, hydroxylated solvents, liquid glycols with low molecular weight and mixtures thereof.

4. Method according to claim 1, characterized in that the protic solvent is used in mixture with an aprotic solvent, the resulting mixture being a protic solvent.

5. Method according to claim 1, characterized in that the protic solvent is distilled or deionized water.

6. Method according to claim 1, characterized in that the at least one aryl diazonium salt correspond to the following formula (I):

$$R-N_2^+, A^- \qquad (I)$$

in which:
A represents a monovalent anion and
R represents an aryl group.

7. Method according to claim 6, characterized in that R is a nitrophenyl radical.

8. Method according to claim 1, characterized in that the radical polymerization primer is selected from the group consisting of phenyl diazonium tetrafluoroborate, 4-nitrophenyl diazonium tetrafluoroborate, 4-bromophenyl diazonium tetrafluoroborate, 2-methyl-4-chlorophenyl diazonium chlorate, 4-benzoylbenzene diazonium tetrafluoroborate, 4-cyanophenyl diazonium tetrafluoroborate, 4-carboxyphenyl diazonium tetrafluoroborate, 4-acetamidophenyl diazonium tetrafluoroborate, 4-phenylacetic acid diazonium tetrafluoroborate, 2-methyl-4-[(2-methylphenyl)diazenyl]benzene diazonium sulfate, 9,10-dioxo-9,10-dihydro-1-anthracene diazonium chloride, 4-nitronaphthalene diazonium tetrafluoroborate and naphthalene diazonium tetrafluoroborate.

9. Method according to claim 1, characterized in that the concentration of the primer within the electrolyte solution is between $10^{-4}$ and 0.5 M.

10. Method according to claim 1, characterized in that the radically polymerizable monomers have a solubility in the said protic solvent which is finite.

11. Method according to claim 1, characterized in that the radically polymerizable monomers are vinyl monomers.

12. Method according to claim 11, characterized in that the vinyl monomers correspond to the following formula (II):

(II)

in which the groups $R_1$ to $R_4$, identical or different, represent a non-metallic monovalent atom selected from the group consisting of an atom of halogen, an atom of hydrogen, a saturated chemical group, and an unsaturated chemical group, said saturated and unsaturated chemical group being selected from an alkyl group, an aryl group, and a —$COOR_5$ group in which $R_5$ represents a hydrogen atom or an alkyl group in $C_1$—$C_6$, nitrile, carbonyl, amine or amide.

13. Method according to claim 12, characterized in that the monomers of formula (II) are selected from the group consisting of acrylonitrile, methacrylonitrile, methyl methacrylate, ethyl methacrylate, butyl methacrylate, propyl methacrylate, hydroxyethyl methacrylate, hydroxypropyl methacrylate, glycidyl methacrylate;

crotononitrile, pentene nitrile, ethyl crotonate and their derivatives; acrylamides selected from the group consisting of aminoethyl, propyl, butyl, pentyl and hexyl methacrylamides;

cyanoacrylates, di-acrylates and di-methacrylates, tri-acrylates and tri-methacrylates, tetra-acrylates and tetra-methacrylates, styrene and its derivatives, parachloro-styrene, pentafluoro-styrene, N-vinyl pyrrolidone, 4-vinyl pyridine, 2-vinyl pyridine, vinyl, acryloyl and methacryloyl halides, and divinylbenzene (DVB).

14. Method according to claim 1, characterized in that the quantity of polymerizable monomer present in the electrolyte solution represents 18 to 40 times the solubility of the said monomer in the protic solvent at a given temperature.

15. Method according to claim 1, characterized in that the quantity of radically polymerizable monomer is between 0.1 M and 5 M.

16. Method according to claim 1, characterized in that the concentration of the surfactant within the electrolyte solution is between 0.5 mM and 5 M.

17. Method according to claim 1, characterized in that the pH of the electrolyte solution is between 1.6 and 2.2.

* * * * *